US00PP36420P3

(12) United States Plant Patent
Knapp et al.

(10) Patent No.: US PP36,420 P3
(45) Date of Patent: Feb. 4, 2025

(54) STRAWBERRY PLANT NAMED 'UC Surfline'

(50) Latin Name: ***Fragaria* x *ananassa* Duchesne.**
Varietal Denomination: UC Surfline

(71) Applicant: The Regents of the University of California, Oakland, CA (US)

(72) Inventors: Steven J. Knapp, Davis, CA (US); Glenn S. Cole, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/135,711

(22) Filed: Apr. 17, 2023

(65) Prior Publication Data

US 2024/0381799 P1 Nov. 14, 2024

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

(56) References Cited

PUBLICATIONS

Cal Poly Strawberry Center 2022 Strawberry Field Day, retrieved online at https://content-calpoly-edu.s3.amazonaws.com/strawberry/1/images/2022Field DayBooklet-FINAL-07_22_22-PM-comp.pdf, 6 introductory pages, pp. 20-29. (Year: 2022).
U.S. Appl. No. 18/135,705, Non-Final Office Action mailed Aug. 29, 2023, 9 pages.

*Primary Examiner* — Susan McCormick Ewoldt
(74) *Attorney, Agent, or Firm* — Kilpatrick Townsend & Stockton LLP

(57) ABSTRACT

'UC Surfline' is a highly productive disease-resistant short-day cultivar that provides high yields in both the early season and late season.

2 Drawing Sheets

Genus and species: The strawberry plant of this invention is botanically known as *Fragaria* x *ananassa* Duchesne.

Variety denomination: The variety denomination is 'UC Surfline'.

BACKGROUND

This invention relates to a new and distinct short-day cultivar of strawberry designated as 'UC Surfline', which originated from a cross performed in the winter of 2016. The plant of this selection was originally designated '16C555P053' for testing.

BRIEF SUMMARY

'UC Surfline' is a 'short-day' cultivar that originated in the winter of 2015-2016 from a cross between proprietary short-day cultivars 07C148P001 and 10C037P604. Clones (daughter plants) of 'UC Surfline' were initially propagated from a single mother plant in 2016-2017. 'UC Surfline' has since been preserved by annual cycles of asexual propagation from stolons in a facility at Winters, California.

'UC Surfline' was selected from a full-sib family (16C555) generated from the cross between 07C148P001 and 10C037P604. It is not known which is the male parent and which is the female parent. Seeds of the 16C555 family were produced and harvested in the spring of 2016 and germinated in June 2016. Seedlings were transplanted to a greenhouse in July 2016, hardened off in a shade house in August 2016, and transplanted to the field in September 2016. 'UC Surfline' was one of 10,000 individual hybrid plants from 121 full-sib families that were grown in 2016-

17. The population was visually phenotyped in the spring of 2018 to: (a) identify individuals with outstanding fruit size, firmness, symmetry, color, gloss, and visual appeal; (b) eliminate individuals with fruit defects and deformities; (c) estimate marketable fruit yields; (d) identify putative photoperiod insensitive individuals; (e) assess stolon proliferation (runner production) and plant architecture; and (f) select individuals for clonal multiplication and further testing. Fifty-six individuals from the 2016-17 selection cycle were selected for on-farm advanced testing in Oxnard, California and Santa Maria, California. Disease resistance of the selections was tested in Davis, California.

'UC Surfline' provides both high early-season and late-season yields, unlike most early short-day cultivars, and is resistant to Fusarium wilt, Verticillium wilt and Phytophthora crown rot, with moderate resistance to Macrophomina. The cultivar flowers from December to early June of the following year in California coastal regions and has moderate winter hardiness as defined by California coastal production measures. 'UC Surfline' also has moderate drought/heat tolerance in California field growing practices.

'UC Surfline' differs from parent and comparison cultivars as follows: 'UC Surfline' is resistant to Fusarium whereas parent 10C037P604 is susceptible. 'UC Surfline' also has moderate resistance to Verticillium and Phytopthora compared to both parent cultivars 07C148P001 and 10C037P604, which are moderately susceptible. 'UC Surfline' is moderately susceptible to Macrophomina, but has improved performance relative to each parent, which are susceptible. 'UC Surfline' provides greater yields in both early and late season compared to 'UCD Victor'(U.S. Plant Pat. No. 32,966) and 'UCD Warrior' (U.S. Plant Pat. No.

32,950). 'UC Surfline' also provides greater yields in the late season compared to 'Fronteras' (U.S. Plant Pat. No. 26,709); and fruit of 'UC Surfline' contains the compounds γ-decalactone, mesifurane, and linalool, which 'Fronteras' lacks.

'UC Surfline' was genotyped with a 50,000-SNP array (Hardigan et. al., *Frontiers in Plant Science* 10:1789, 2020; Hardigan et. al., *Mol. Biol. Evol.* 38:2285-2305, 2021) that included 72 cultivars owned by the Applicant and 300 publicly available cultivars not owned by the Applicant. After quality-and LD-pruning, 31,212 SNP markers with well-separated codominant genotypic clusters were selected for further analysis. These analyses confirmed that 'UC Surfline' is genetically distinct from its parent varieties, and comparison varieties 'UC Monarch' (U.S. Plant patent application Ser. No. 18/135,707, filed Apr. 17, 2023), 'UCD Victor', and 'Fronteras', as well as all of the other cultivars evaluated.

BRIEF DESCRIPTION OF THE DRAWINGS

The colors in the photographs are depicted as nearly true as is reasonably possible to obtain in color reproductions of this type.

DETAILED DESCRIPTION

Botanical Description

Figure 1:
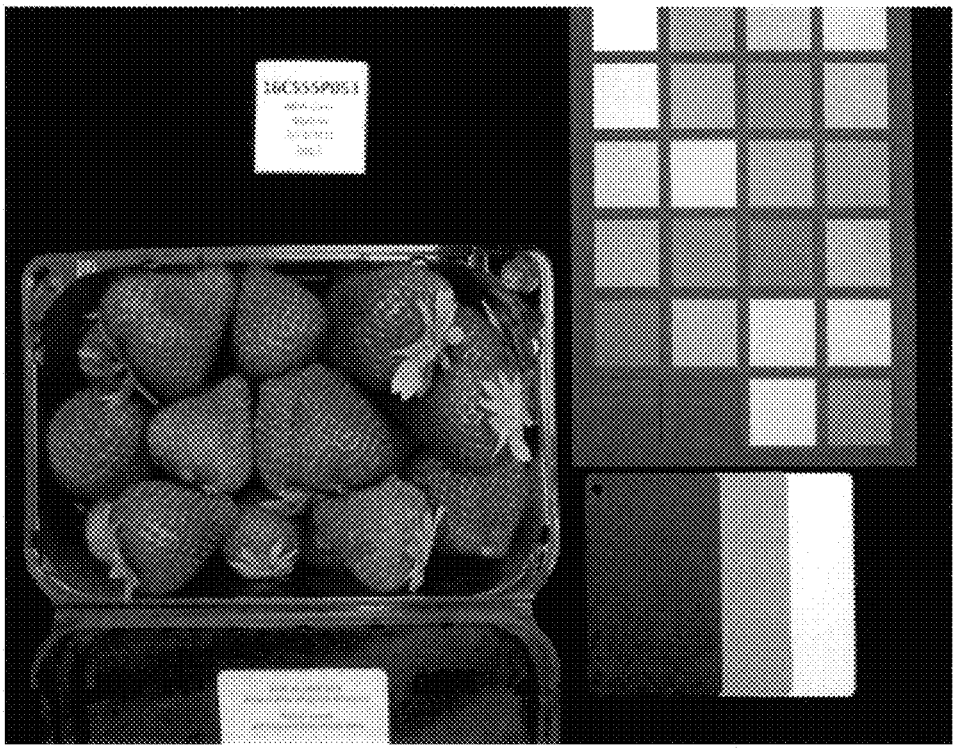
FIG. 1 depicts fruit of 'UC Surfline'.
Figure 2:
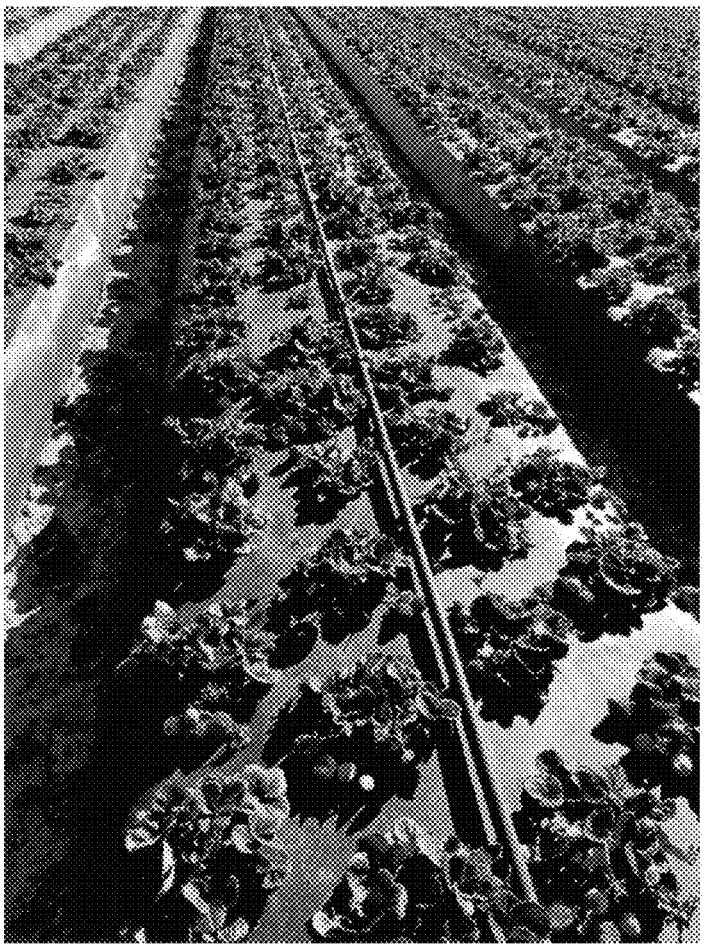
FIG. 2 shows 'UC Surfline' plants.

Botanical descriptors of 'UC Surfline' are provided in Table 1. The descriptors were collected in the spring and summer of 2022 from plants grown in Santa Maria, California. Colors are designated with reference to The Royal Horticultural Society (RHS) Colour Chart, Sixth Edition, 2015. The characteristics of 'UC Surfline' may vary in detail, depending upon environmental factors and culture conditions.

TABLE 1

[a]Mean values were estimated from nine samples per trait.

| Category | Trait | Unit | Range (Mean[a]) or Color (RHS Color Designation) |
|---|---|---|---|
| Foliar | Plant height | mm | 230-290 (258) |
| Foliar | Plant spread | mm | 420-500 (461) |
| Foliar | Mid-tier leaflet length | mm | 85-110 (100) |
| Foliar | Mid-tier leaflet width | mm | 105-150 (125) |
| Foliar | Leaf venation | | Compound Simple Pinnate |
| Foliar | Leaf margin | | Dentate |
| Foliar | Leaf texture | | Medium blistering and glossiness |
| Foliar | Petiole length | mm | 210-270 (246) |
| Foliar | Petiole diameter | mm | 2.78 |
| Foliar | Petiole color | color code | Strong Yellow Green (144 B) |
| Foliar | Stipule core color | color code | Strong Yellow Green (144 A) |
| Foliar | Stipule margin color | color code | Strong Yellow Green (143 A) |
| Foliar | Stolons/nursery mother plant | count | 14-16 (15) |
| Foliar | Stolon length | cm | 75 |
| Foliar | Stolon diameter | mm | 2 |
| Foliar | Stolon color | color code | Strong Red (51 A) |

TABLE 1-continued

[a]Mean values were estimated from nine samples per trait.

| Category | Trait | Unit | Range (Mean[a]) or Color (RHS Color Designation) |
|---|---|---|---|
| Foliar | Leaf color, adaxial | color code | Moderate Olive Green (147 A) |
| Foliar | Leaf color, abaxial | color code | Moderate Yellow Green (147 B) |
| Pedicel | Pedicel color | color code | Strong Yellow Green (144 B) |
| Pedicel | Pedicel length | mm | 132 |
| Pedicel | Pedicel diameter | mm | 3 |
| Flower | Petal number | count | 5-8 (7) |
| Flower | Petal length | mm | 10-16 (11) |
| Flower | Petal width | mm | 10-16 (11) |
| Flower | Petal apex shape | | Rounded/Convex |
| Flower | Petal base shape | | Obtuse |
| Flower | Petal margin shape | | Smooth |
| Flower | Calyx diameter | mm | 28-53 (38) |
| Flower | Corolla diameter | mm | 20-39 (28) |
| Flower | Sepal number | count | 10-16 (13) |
| Flower | Sepal length | mm | 21 |
| Flower | Sepal width | mm | 11 |
| Flower | Calyx Color | color code | Moderate Olive Green (146 A) |
| Flower | Upper Petal Color | color code | White (NN155 D) |
| Flower | Lower Petal Color | color code | White (NN155 D) |
| Flower | Stamen number | count | 24-38 (32) |
| Fruit | Achene Color | color code | Greenish Brilliant Yellow (4 A) |
| Fruit | Fruit length | mm | 38-47 (43) |
| Fruit | Fruit width | mm | 32-46 (39) |
| Fruit | Fruit shape | | Cordate |
| Fruit | Size of hollow core | mm | 0-8 (2) |
| Fruit | External Fruit (exterior) color | color code | Moderate Red (N45 A) |
| Fruit | Fruit flesh color | color code | Strong Reddish Orange (42 B) |
| Fruit | Fruit core color | color code | Strong Reddish Orange (42 C) |
| Fruit | Fruit weight | g/fruit | 21-38 (30) |

Disease Resistance

'UC Surfline' and comparison cultivars were phenotyped for resistance to Fusarium wilt, Verticillium wilt, Phytophthora crown rot (PhCR), and Macrophomina over three growing seasons in Davis, California. Hybrids were screened using bare-root plants (four clones/hybrid) that were artificially inoculated with a single pathogen, planted in fumigated ground in November, and phenotyped for disease symptoms in late spring and early summer using established protocols.

The disease resistance scores for 'UC Surfline' were primarily compared to those for 'Fronteras', 'UCD Victor', 'UCD Warrior', and 'San Andreas' (U.S. Plant Pat. No. 19,975). Estimated marginal means (EMMs), linear contrasts among EMMs for 'UC Surfline', and comparison cultivars and associated statistics from three seasons of disease screening in Davis, CA are shown in Table 2.

'UC Surfline' and the comparison cultivars were resistant to Fusarium wilt race 1(Table 2). 'UC Surfline' is heterozygous for FW1, a dominant gene that confers resistance to race 1 isolates of *Fusarium oxysporum* f. sp. *fragariae*. This was confirmed using DNA markers in linkage disequilibrium with FW1 and validated by three years of field testing (Table 2).

'UC Surfline' is also resistant to Verticillium Wilt and Phytophthora crown rot in these disease screening trials (Table 2). Scores for 'UC Surfline' for Verticillium Wilt, Phytophthora Crown Rot, and Macrophomina charcoal rot resistance have been among the strongest observed high yielding cultivars.

The Macrophomina resistance score EMMs reported in Table 2 were estimated from phenotypes observed in a high heat and drought stress environment (Davis, CA). Although the resistance score EMM for 'UC Surfline' from abiotic stress environment was intermediate (3.61), this generally translates to a resistance score in the 1.5 to 2.5 range in coastal CA production environments. No Macrophomina disease symptoms were observed on 'UC Surfline' from natural Macrophomina infections in any of the on-farm trials. The Macrophomina resistance of 'UC Surfline' is as strong as that found in any commercially important short-day cultivar today.

TABLE 2

Across year estimated-marginal means (EMMs) for *Fusarium* wilt, *Verticillium* wilt, *Phytophthora* crown rot (PhCR), and *Macrophomina* resistance scores[a] for 'UC Surfline' and comparison cultivars observed in 2019-20, 2020-21, and 2021-22 disease resistance screening trials in Davis, California

| Disease[b] | Comparison Cultivar | UC Surfline EMM | Comparison Cultivar EMM | t[c] | p-value[d] |
|---|---|---|---|---|---|
| *Fusarium* Wilt | Fronteras | 1.02 | 1.09 | −0.18 | 0.86 |
| | UCD Victor | | 1.09 | −0.17 | 0.87 |
| | UC Monarch | | 1.22 | −0.47 | 0.64 |
| | UCD Warrior | | 1.47 | −0.98 | 0.33 |
| | San Andreas | | 1.15 | −0.27 | 0.79 |
| *Verticillium* Wilt | Fronteras | 1.62 | 1.71 | −0.19 | 0.85 |
| | UCD Victor | | 2.30 | −1.58 | 0.12 |
| | UC Monarch | | 1.79 | −0.39 | 0.70 |
| | UCD Warrior | | 2.56 | −2.23 | 0.03 |
| | San Andreas | | 1.29 | 0.50 | 0.62 |
| *Phytophthora* Crown Rot | Fronteras | 1.67 | 2.54 | −1.68 | 0.10 |
| | UCD Victor | | 2.19 | −0.99 | 0.33 |
| | UC Monarch | | 2.04 | −0.66 | 0.51 |
| | UCD Warrior | | 2.03 | −0.68 | 0.50 |
| | San Andreas | | 1.83 | −0.24 | 0.81 |
| *Macrophomina* | Fronteras | 3.61 | 4.16 | −0.89 | 0.38 |
| | UC Victor | | 4.50 | −1.43 | 0.16 |
| | UC Monarch | | 3.62 | −0.03 | 0.98 |
| | UC Warrior | | 3.78 | −0.28 | 0.78 |
| | San Andreas | | 4.71 | −1.26 | 0.26 |

[a]The ordinal symptom rating scales were identical for each disease: 1 = highly resistant, 2 = moderately resistant, 3 = moderately susceptible, 4 = susceptible, and 5 = highly susceptible.
[b]The fungal pathogens causing these diseases are *Fusarium oxysporum* f. sp. *fragariae* (*Fusarium* wilt), *Verticillium dahliae* (*Verticillium* wilt), *Phytophthora cactorum* (*Phytophthora* crown rot), and *Macrophomina phaseolina*.
[c]t-statistics for linear contrasts between EMMs for 'UC Surfline' and comparison cultivars ($EMM_1$-$EMM_2$).
[d]The probability of a greater t-statistic by chance for tests of the null hypothesis of no difference between EMMs ($H_0$: $EMM_1 = EMM_2$).

Field Evaluations

Three seasons of advanced testing of selected short-day hybrids originating from the 2015-16 breeding cycle, starting with 112 in 2018-19 and finishing with three, one of which was 'UC Surfline', in 2020-21 were completed. Comparison cultivars were 'Fronteras' and 'UCD Victor'.

Clones (asexually propagated bare-root plants) for the first year of testing (Phase 1 in 2017-18) were produced in Winters, California. Clones for subsequent years of testing (Phase 2 in 2019-20 and 2020-21 and Phase 3 in 2012-22 and 2022-23) were produced in commercial high-elevation nurseries (Dorris, California) using standard production and propagation practices and post-harvest chilling treatments optimized for the short-day market segment. Clones were harvested in September, trimmed, and directly planted in October of each year.

For on-farm yield trials, plants were grown in two 12-plant plots in Phase 1 yield trials, two 24-plant plots in Phase 2 yield trials, and two 500- or 1,000-plant strips in Phase 3 yield trials. The plots were arranged in randomized complete blocks experiment designs in commercial production fields. These experiments were grown using the management practices, bed configurations, plastic mulches, planting densities, planting dates, irrigation, fertilization, and pesticide application decisions and schedules, and harvest schedules of our cooperators.

The number of harvests ranged from 14 to 37 in each yield trial. Marketable fruit yield, count, and size were recorded at each harvest. Collection and analysis of 4,695 observations were employed for these traits to support statistical analyses and selection decisions.

Fruit Quality

Fruit from early and peak season harvests from every trial were evaluated to phenotype fruit for firmness, total soluble solids (TSS=Brix), and titratable acidity (TA). Over three growing seasons, 2,240 observations were collected for fruit quality traits at harvest to support statistical analyses and selection decisions.

Plants were assessed for flavor and aroma through informal hedonic testing in the field and laboratory by various individuals, including growers, shippers, and others. Although specific volatile organic compounds (VOCs) known to affect aroma were not selected for, selection pressure for enhanced flavor and aroma was applied and VOC profiles were analyzed for 152 cultivars and other hybrids over two years of on-farm testing. 'UC Surfline' was among the hybrids phenotyped for VOC. These data were used to assess the effect of subjective olfactory and gustatory assessments on aroma profile changes. VOC analyses were performed using solid phase microextraction (SPME) gas chromatography-mass spectroscopy of fruit samples collected from early and peak season harvests over two years from on-farm yield trials in Santa Maria and Oxnard, California. Although at least 360 VOCs have been identified in developing strawberry receptacles, aroma and flavor are dominated by fewer than 10. Data for approximately 44 VOCs affecting aroma (45,364 phenotypic observations) were collected and analyzed to support statistical analyses. Data for three VOCs (γ-decalactone, mesifurane, and linalool) that are predicted to contribute towards the improved flavor of 'UC Surfline' are provided.

'UC Surfline' equals or exceeds the fruit quality and shelf life standards of long shelf life (LSL) strawberries designed for prolonged cold storage and long-distance shipping and production in the short-day market segment. Table 3 provides estimated marginal means (EMMs), linear contrasts among EMMs for 'UC Surfline' and comparison cultivars ('Fronteras', 'UCD Victor', and 'UC Monarch'), and associated statistics within and between environments (2 locations×3 years). 'UC Surfline' produced significantly firmer fruit than 'Fronteras' across farms and years ($p$=0.001). No significant differences were observed in total soluble solids (TS)), titratable acidity (TA), or TSS/TA ratio between 'UC Surfline' and the comparison cultivars, apart from TA, which was significantly greater for 'UC Surfline' than 'UC Victor' (Table 3).

The aroma of 'UC Surfline' is more noticeable than that of 'Fronteras'. Three volatile organic compounds (VOCs) are important components of strawberry aroma: γ-decalactone, mesifurane, and linalool. All three were found in 'UC Surfline', which contributed to the more pronounced aroma and flavor profile of 'UC Surfline' (Table 4).

'UC Surfline' meets the shelf life requirements for mass-produced cultivars developed for cold storage and long-distance shipping in California. Minimal declines in the deterioration of fruit firmness and other fruit quality traits were observed over 14 days of post-harvest cold storage using fruit sampled from peak and late season harvests. No statistically significant differences were observed for leakage, gloss, TSS, TA, mold, or other post-harvest traits between 'UC Surfline' and the comparison cultivars.

TABLE 3

Across-environment estimated marginal means (EMMs) for cumulative marketable fruit yield and other fruit traits for 'UC Surfline' and comparison cultivars grown on commercial farms in Oxnard and Santa Maria, CA over three growing seasons (2019-20 to 2021-22).

| Trait[a] | Comparison Cultivar | 'UC Surfline' EMM | Comparison Cultivar EMM | t[b] | p-value[c] |
|---|---|---|---|---|---|
| Early Yield(lb/acre)[d] | Fronteras | 6,383 | 5,334 | 1.75 | 0.10 |
| | UCD Victor | | 2,401 | 6.15 | <0.0001 |
| Yield (lb/acre) | Fronteras | 46,868 | 38,833 | 2.18 | 0.05 |
| | UCD Victor | | 40,874 | 1.51 | 0.15 |
| Size (g/fruit) | Fronteras | 29.5 | 32.4 | −2.61 | 0.03 |
| | UCD Victor | | 29.6 | −0.07 | 0.94 |
| Firmness (g-force) | Fronteras | 339.1 | 225.9 | 3.44 | 0.001 |
| | UCD Victor | | 296.5 | 1.64 | 0.11 |
| TSS (%) | Fronteras | 8.18 | 8.67 | −1.25 | 0.22 |
| | UCD Victor | | 7.89 | 0.97 | 0.34 |
| TA (%) | Fronteras | 0.86 | 0.86 | 0.11 | 0.91 |
| | UCD Victor | | 0.76 | 2.93 | 0.005 |
| TSS/TA | Fronteras | 9.82 | 10.44 | −0.87 | 0.39 |
| | UCD Victor | | 10.47 | −1.15 | 0.26 |

[a]Cumulative marketable fruit yields were estimated from fruit harvested on commercial schedules (once or twice weekly) over the entire short-day growing season on each farm. Fruit firmness, total soluble solids (TSS), and titratable acidity (TA) were measured from multiple fruit/replication sampled from two harvests/trial. EMMs and test statistics were estimated from the phenotypes of fruit harvested from two 24-plant plots/entry/environment.
[b]t-statistics for linear contrasts ($EMM_1$-$EMM_2$) between 'UC Surfline' and comparison cultivar EMMs.
[c]The probability of a greater t-statistic by chance for tests of the null hypothesis of no difference between EMMs ($H_0$: $EMM_1 = EMM_2$).
[d]Cumulative marketable fruit yield from first harvest.

TABLE 4

Across-year estimated-marginal means (EMMs) for γ-decalactone, mesifurane, and linalool concentrations[a] in ripe fruit of 'UC Surfline' and comparison cultivars harvested in 2020-21 and 2021-22 from on-farm yield trials in Nipomo, CA.

| Cultivar | γ-decalactone EMM | mesifurane EMM | linalool EMM |
|---|---|---|---|
| Fronteras | 0 | 0 | 0 |
| UC Victor | 0 | 4,181 | 100,499 |
| UC Monarch | 36,429 | 23,660 | 65,017 |

TABLE 4-continued

Across-year estimated-marginal means (EMMs) for γ-decalactone, mesifurane, and linalool concentrations[a] in ripe fruit of 'UC Surfline' and comparison cultivars harvested in 2020-21 and 2021-22 from on-farm yield trials in Nipomo, CA.

| Cultivar | γ-decalactone EMM | mesifurane EMM | linalool EMM |
|---|---|---|---|
| UC Surfline | 7,555 | 2,792 | 93,371 |
| LSD[b] | 42,528 | 18,116 | 66,721 |

[a]The relative concentrations of volatile organic compounds (ng/g dry weight) were estimated from the raw solid phase microextraction (SPME) GC-MS data (peak area in counts) and normalized samples.
[b]Least significant differences are shown for a false-positive probability of p = 0.05.

Fruit Production Characteristics—Field Trials

The number of harvests ranged from 14 to 37 in each trial to assess 'UC Surfline' fruit production. Marketable fruit yield, count, and size were recorded at each harvest. Collection and analysis of 4,695 observations were performed for these traits to support statistical analyses and selection decisions.

Statistics are shown for linear contrasts between the estimated marginal means (EMMs) for 'UC Surfline', and comparison cultivars across environment (2 locations×3 years) and for individual environments to highlight variation in planting dates, the number of harvests, harvest ranges, and production practices (Table 5). EMMs were estimated from two 24-plant plots (replications)/entry/environment in 2020 and 2021.

TABLE 5

Within environment estimated marginal means (EMMs) for cumulative marketable fruit yield for early season harvests (before March 1) 'UC Surfline' and comparison cultivars grown on farms in coastal California over three growing seasons (2019-20 to 2021-22)[a].

| Location | Season | Comparison Cultivar | UC Surfline EMM (lb/a) | Cultivar EMM Comparison (lb/a) | t[b] | p-value[c] |
|---|---|---|---|---|---|---|
| Oxnard | 2019-20 | Fronteras | 6,851 | 6,081 | 0.29 | 0.80 |
| | | UCD Victor | | 2,958 | 1.44 | 0.29 |
| Santa Maria | 2019-20 | Fronteras | 2,696 | 2,680 | 0.02 | 0.99 |
| | | UCD Victor | | 577 | 1.91 | 0.09 |
| Oxnard | 2020-21 | Fronteras | 9,622 | 6,558 | 1.65 | 0.20 |
| | | UCD Victor | | 5,073 | 2.45 | 0.09 |
| Santa Maria | 2020-21 | Fronteras | 9,107 | 4,571 | 6.28 | 0.01 |
| | | UCD Victor | | 1,037 | 11.17 | 0.002 |
| Oxnard | 2021-22 | Fronteras | 7,246 | 8,392 | −1.33 | 0.28 |
| | | UCD Victor | | 4,010 | 3.76 | 0.03 |
| Santa Maria | 2021-22 | Fronteras | 6,107 | 5,765 | 0.62 | 0.58 |
| | | UCD Victor | | 2,892 | 5.86 | 0.01 |

[a]Linear contrasts between estimated marginal means (EMMs) for 'UC Surfline' and comparison cultivars were estimated for each environment (location × year). Cumulative marketable fruit yields were estimated from fruit harvested on commercial schedules (once or twice weekly) from the start of harvest through March 1. EMMs and test statistics were estimated from the phenotypes of fruit harvested from two 24-plant plots/entry.
[b]t-statistics for linear contrasts ($EMM_1$-$EMM_2$) between the EMMs for 'UC Surfline' and comparison cultivars.
[c]The probability of a greater t-statistic by chance for tests of the null hypothesis of no difference between EMMs ($H_0$: $EMM_1 = EMM_2$).

'UC Surfline' is highly competitive for early season yield. The early yields of 'UC Surfline' were not significantly different from 'Fronteras' for any of the three growing seasons in Oxnard (Table 5). The early yield of 'UC Surfline' was significantly greater than 'UCD Victor' in 2021-22, but was not significantly different from 'UCD Victor' in the other two growing seasons (Table 5).

'UC Surfline' is thus a highly productive disease resistant short-day cultivar that provides high yields in both the early season and late season. The fruit is suitable for both fresh market use and processing purposes.

What is claimed is:

1. A new and distinct cultivar of strawberry plant having the characteristics substantially as described and illustrated herein.

* * * * *